United States Patent
Ferber et al.

(10) Patent No.: US 7,419,475 B2
(45) Date of Patent: Sep. 2, 2008

(54) BODY MASSAGER WITH ILLUMINATION EFFECTS

(75) Inventors: Roman Ferber, West Bloomfield, MI (US); Huang Wen Wei, Fujian (CN)

(73) Assignee: FKA Distibuting Co., Commerce Township, MI (US)

( * ) Notice: Subject to any disclaimer, the term of this patent is extended or adjusted under 35 U.S.C. 154(b) by 344 days.

(21) Appl. No.: 11/223,685

(22) Filed: Sep. 9, 2005

(65) Prior Publication Data

US 2007/0060851 A1 Mar. 15, 2007

(51) Int. Cl.
A61H 1/00 (2006.01)
A61H 7/00 (2006.01)
A61H 15/00 (2006.01)

(52) U.S. Cl. .............................. 601/99; 601/15; 601/46; 601/49; 601/90; 601/94; 601/116; 601/134; 601/89; 601/97

(58) Field of Classification Search .................... 601/15, 601/46, 49, 84, 89, 90, 91–94, 97, 98, 99, 601/100–103, 115, 116, 134

See application file for complete search history.

(56) References Cited

U.S. PATENT DOCUMENTS

| | | | |
|---|---|---|---|
| 2,097,455 A | 11/1937 | Fisher | |
| 3,001,523 A | 9/1961 | Sugimoto | |
| 3,374,784 A | 3/1968 | Brent et al. | |
| 3,633,571 A | 1/1972 | Shinagawa | |
| 4,167,182 A | 9/1979 | Yamamura et al. | |
| 4,373,516 A | 2/1983 | Masuda et al. | |
| 4,412,534 A | 11/1983 | Hamabe et al. | |
| 4,422,448 A | 12/1983 | Sugai et al. | |
| 4,422,449 A | 12/1983 | Hamabe | |
| 4,491,127 A | 1/1985 | Yamamura et al. | |
| 4,505,267 A | 3/1985 | Inada | |
| 4,574,786 A | 3/1986 | Hashimoto et al. | |
| 4,576,149 A | 3/1986 | Otuka et al. | |
| 4,686,967 A | 8/1987 | Hashimoto et al. | |
| 4,718,408 A | 1/1988 | Barreiro | |
| 5,020,518 A | 6/1991 | Spears et al. | |

(Continued)

FOREIGN PATENT DOCUMENTS

EP 1400230 A1 9/2002

(Continued)

OTHER PUBLICATIONS

Dr. Scholl's, Look. Feel. Do. Better., 2003, Helen of Troy.

(Continued)

*Primary Examiner*—Justine R Yu
*Assistant Examiner*—Annette F Dixon
(74) *Attorney, Agent, or Firm*—Brooks Kushman P.C.

(57) ABSTRACT

The present invention discloses a massage apparatus having a housing with a massage formation for contacting a body part of a user. A massage mechanism is oriented within the housing for imparting a massage effect to the massage formation. A light source is provided on the massage formation for conveying an illumination effect from the massage formation. A partially translucent massager is disclosed for providing a visual effect of the underlying massage operation. Further, a roller massage assembly is provided wherein a load imparted to a roller is distributed directly to a structure of the massager for preventing distribution of the load to the massage mechanism.

13 Claims, 9 Drawing Sheets

U.S. PATENT DOCUMENTS

| | | | |
|---|---|---|---|
| 5,179,940 A | 1/1993 | Barreiro | |
| 5,233,973 A | 8/1993 | Gill et al. | |
| 5,265,590 A | 11/1993 | Takagi | |
| 5,460,598 A | 10/1995 | Yamasaki et al. | |
| 5,462,516 A | 10/1995 | Anderson | |
| 5,464,382 A | 11/1995 | Wang | |
| 5,630,790 A | 5/1997 | Ito | |
| 5,755,677 A | 5/1998 | Masuda et al. | |
| 5,792,080 A | 8/1998 | Ookawa et al. | |
| 5,807,288 A | 9/1998 | Wu | |
| 6,039,679 A | 3/2000 | Yu | |
| 6,056,708 A | 5/2000 | Sayama et al. | |
| 6,077,238 A | 6/2000 | Chung | |
| 6,083,180 A | 7/2000 | Shimizu | |
| 6,110,102 A * | 8/2000 | Harrison | 601/46 |
| 6,200,282 B1 | 3/2001 | Furuie et al. | |
| 6,213,962 B1 | 4/2001 | Shimizu | |
| 6,224,563 B1 | 5/2001 | Nonoue et al. | |
| 6,283,928 B1 | 9/2001 | Wang | |
| 6,312,400 B1 | 11/2001 | Itikawa et al. | |
| 6,394,970 B1 * | 5/2002 | Maier | 601/99 |
| 6,402,709 B1 | 6/2002 | Wu | |
| 6,494,851 B1 | 12/2002 | Becher | |
| 6,503,212 B2 | 1/2003 | Park | |
| 6,511,448 B1 | 1/2003 | Furuie et al. | |
| 6,517,500 B2 | 2/2003 | Ichikawa | |
| 6,629,939 B2 * | 10/2003 | Jikiba et al. | 601/99 |
| 6,656,140 B2 | 12/2003 | Oguma et al. | |
| 6,749,577 B2 | 6/2004 | Kume et al. | |
| 6,786,555 B2 | 9/2004 | Brook | |
| 6,790,190 B2 | 9/2004 | Marcantoni | |
| 6,805,680 B2 | 10/2004 | Klingler | |
| 6,808,500 B1 | 10/2004 | Cheng-Yi et al. | |
| 6,814,709 B2 | 11/2004 | Schwartz et al. | |
| 6,814,710 B1 | 11/2004 | Dehli | |
| 6,832,991 B1 | 12/2004 | Inada et al. | |
| 6,837,861 B2 | 1/2005 | Lin | |
| 6,840,914 B1 | 1/2005 | Takamura | |
| 6,849,054 B1 | 2/2005 | Kim | |
| 6,890,313 B2 | 5/2005 | Kim | |
| 6,899,688 B2 | 5/2005 | Wu | |
| 6,911,012 B2 | 6/2005 | Kahn | |
| 6,916,300 B2 | 7/2005 | Hester et al. | |
| 6,979,300 B1 * | 12/2005 | Julian et al. | 601/15 |
| 6,991,609 B2 * | 1/2006 | Kan et al. | 601/99 |
| 7,001,347 B2 * | 2/2006 | Furuie | 601/98 |
| 7,128,721 B2 | 10/2006 | Ferber et al. | |
| 2002/0138023 A1 | 9/2002 | Kume et al. | |
| 2003/0018284 A1 | 1/2003 | Lim | |
| 2003/0032903 A1 | 2/2003 | Kasai | |
| 2003/0060741 A1 | 3/2003 | Park | |
| 2003/0120187 A1 | 6/2003 | Kan et al. | |
| 2003/0212353 A1 | 11/2003 | Kahn | |
| 2003/0212354 A1 | 11/2003 | Kahn | |
| 2003/0216673 A1 | 11/2003 | Miki et al. | |
| 2003/0216674 A1 | 11/2003 | Miki et al. | |
| 2003/0225351 A1 | 12/2003 | Wu | |
| 2004/0049136 A1 | 3/2004 | Lin | |
| 2004/0082889 A1 | 4/2004 | Wu | |
| 2004/0097851 A1 | 5/2004 | Inada et al. | |
| 2004/0106882 A1 | 6/2004 | Tseng | |
| 2004/0122343 A1 | 6/2004 | Mori et al. | |
| 2004/0127823 A1 | 7/2004 | Mori et al. | |
| 2004/0158176 A1 | 8/2004 | Park | |
| 2004/0158180 A1 | 8/2004 | Liang | |
| 2004/0171972 A1 | 9/2004 | Shimizu et al. | |
| 2004/0183345 A1 | 9/2004 | Furuie et al. | |
| 2004/0186398 A1 | 9/2004 | Furuie | |
| 2004/0210174 A1 | 10/2004 | Kim | |
| 2004/0211015 A1 | 10/2004 | Chen | |
| 2004/0225240 A1 | 11/2004 | Kim | |
| 2004/0230145 A1 | 11/2004 | Kim | |
| 2004/0236256 A1 | 11/2004 | Kim | |
| 2004/0243030 A1 | 12/2004 | Tanizawa et al. | |
| 2004/0243033 A1 | 12/2004 | Kim | |
| 2004/0243034 A1 | 12/2004 | Kim | |
| 2004/0249321 A1 | 12/2004 | Grueger et al. | |
| 2004/0260215 A1 | 12/2004 | Kim | |
| 2005/0010142 A1 | 1/2005 | Kim | |
| 2005/0010143 A1 | 1/2005 | Kim | |
| 2005/0010144 A1 | 1/2005 | Chen | |
| 2005/0015029 A1 | 1/2005 | Kim | |
| 2005/0033204 A1 | 2/2005 | Nakamura et al. | |
| 2005/0049530 A1 | 3/2005 | Kim | |
| 2005/0049531 A1 | 3/2005 | Kim | |
| 2005/0080365 A1 | 4/2005 | Wu et al. | |
| 2005/0090770 A1 | 4/2005 | Chen | |
| 2005/0090771 A1 | 4/2005 | Miki | |
| 2005/0096571 A1 | 5/2005 | Miki | |
| 2005/0101890 A1 | 5/2005 | Mizoguchi et al. | |
| 2005/0137503 A1 | 6/2005 | Hori et al. | |
| 2005/0148912 A1 | 7/2005 | Liao | |
| 2005/0209539 A1 | 9/2005 | Lev et al. | |
| 2005/0245851 A1 | 11/2005 | Ferber et al. | |
| 2005/0256434 A1 | 11/2005 | Luo | |

FOREIGN PATENT DOCUMENTS

| | | |
|---|---|---|
| GB | 2 123 298 A | 2/1984 |
| GB | 2 267 440 A | 12/1993 |
| JP | S50-86889 A | 7/1975 |
| JP | S56-119251 A | 9/1981 |
| JP | S59-28963 A | 2/1984 |
| JP | S60-135122 U | 9/1985 |
| JP | H06-209974 A | 8/1994 |
| JP | H07-080035 A | 3/1995 |
| JP | H10-216187 A | 8/1998 |
| JP | 2000-262575 A | 9/2000 |
| JP | 2001-17494 A | 1/2001 |
| JP | 2001-29419 A | 2/2001 |
| JP | 2001-314470 A | 11/2001 |
| JP | 2001-314471 A | 11/2001 |
| JP | 2002-263155 A | 9/2002 |
| JP | 2003-38591 A | 2/2003 |
| WO | 02069880 A1 | 9/2002 |

OTHER PUBLICATIONS

HoMedics, Shiatsu Massaging Cushion, Moving Massage Mechanism, SBM-200, Instruction Manual and Warranty Information, 2003-2005 HoMedics, Inc., 15 pgs.

HoMedics, Float™, Massaging Waterbed for the Feet, FM-H20, Instruction Manual and Warranty Information, 2004 HoMedics, Inc., 7 pgs.

Office Action and pending claims for U.S. Appl. No. 11/082,074, mailed Sep. 19, 2007, 23 pages.

Patent Cooperation Treaty International Search Report and Written Opinion for related application PCT/US06/31051, mailed Feb. 20, 2007, 10 pages.

HoMedics, Shiatsu Massaging Cushion, Moving Massage Mechanism, SBM-200, Instruction Manual and Warranty Information, 2003-2005 HoMedics, Inc., and Figures from Ferber et al. 7,128,721 B2, 20 pages.

* cited by examiner

BODY MASSAGER WITH ILLUMINATION EFFECTS

BACKGROUND OF THE INVENTION

1. Field of the Invention

The present invention relates to massagers.

2. Background Art

The prior art includes massagers that provide various massage functions. Quite often, these massage functions are not readily viewable at a point of sale. In order to inform a consumer of the massage functions of various massagers, inspection of the massager may be required by the consumer, or displays or advertising may convey information about the product to a consumer.

Often times, products such as massagers are provided on display outside of the packaging for testing by consumers. In massagers, wherein the massage features are not readily visible, inspection of the massager by the consumer, or actual use of the massager by the consumer may be required in order to inform the consumer of the massage effects provided by the massager.

The prior art has provided massagers wherein a pair of rollers are provided on an arm of a massage mechanism. Typically, such rollers are provided with biasing members for maintaining the roller arm in an unloaded position.

A goal of the present invention is to provide a massager having improved massage features in view of the prior art.

SUMMARY OF THE INVENTION

In one non-limiting embodiment of the invention, a massage apparatus is provided with a housing, a massage formation on the housing for contacting a body part, and a massage mechanism within the housing for imparting a massage effect in the massage formation. A light source is provided on the massage formation for conveying an illumination effect.

In one non-limiting embodiment of the invention, a body massager is provided with a housing, a guide mounted in the housing, a carriage oriented in the housing in cooperating with the guide for translation in the housing, and a motor oriented in the housing for translating the carriage along the guide. Massage members are mounted to the carriage for providing a massage effect to the user. The housing is partially translucent so that a user may view the massage members.

In another non-limiting embodiment of the invention, a body massager is provided with a housing, a longitudinal guide in the housing, a carriage oriented in the housing, and a first motor within the housing. A second motor is provided in the housing for driving a transverse shaft which imparts oscillation to a pair of massage brackets. A massage arm is mounted to each massage bracket and a pair of massage arms are each pivotally connected to one of the massage brackets. A pair of massage rollers are mounted to each massage arm for oscillation relative to the carriage. Upon application of a load to the massage rollers, the massage rollers engage the carriage for distributing the load directly to the carriage.

The above objects and other objects, aspects, features and advantages of the present invention are readily apparent from the following detailed description of the preferred embodiment for carrying out the invention when taken in connection with the accompanying brief description of the drawings.

DETAILED DESCRIPTION OF EMBODIMENTS OF THE INVENTION

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated of minimized to show details of particular components. Therefore, specific structural and functional details disclosed herein are not to be interpreted as limiting, but merely as a representative basis for the claims and/or as a representative basis for teaching one skilled in the art to variously employ the present invention.

Figure 1:
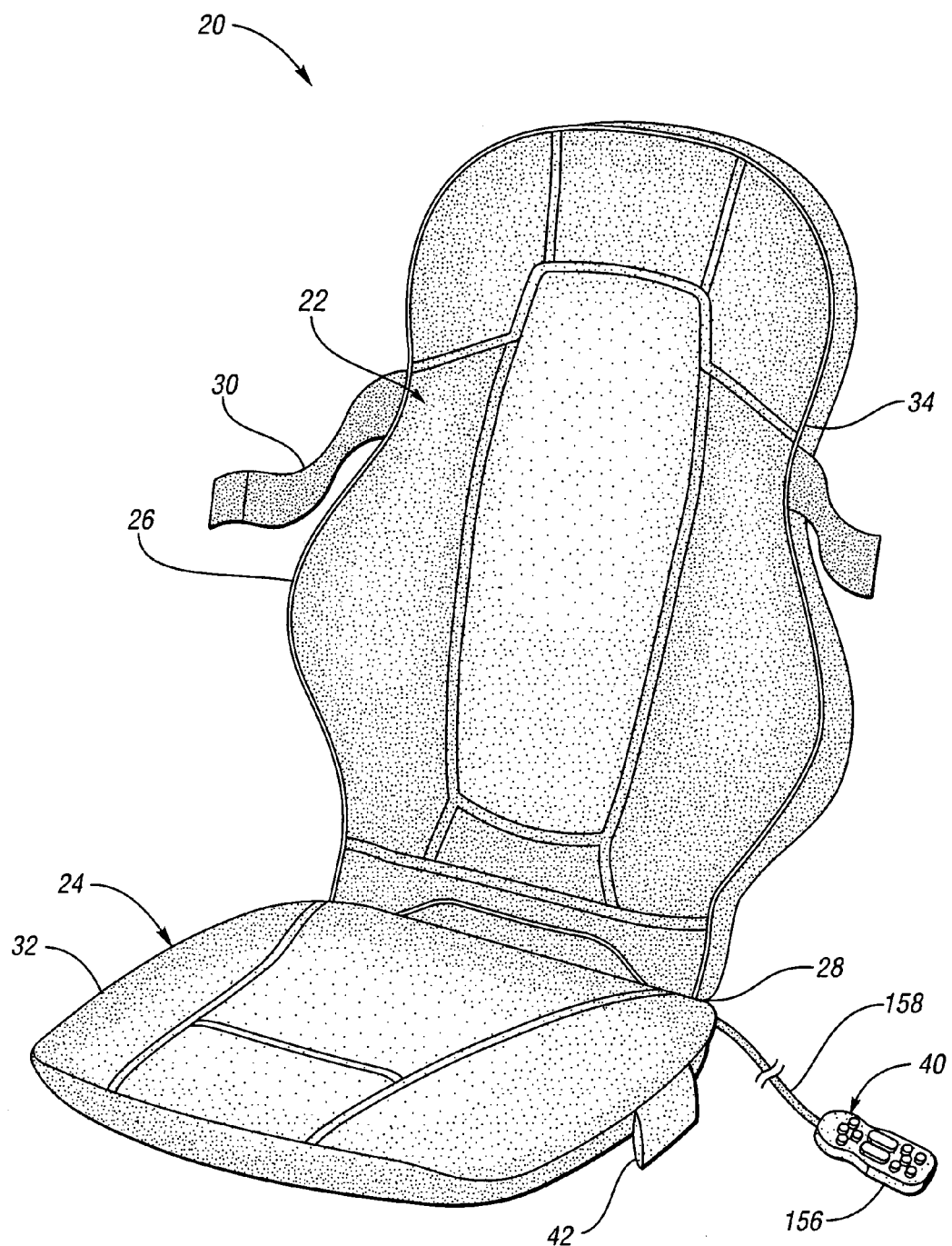
FIG. 1 is a perspective view of a massager in accordance with the present invention.
Figure 2:
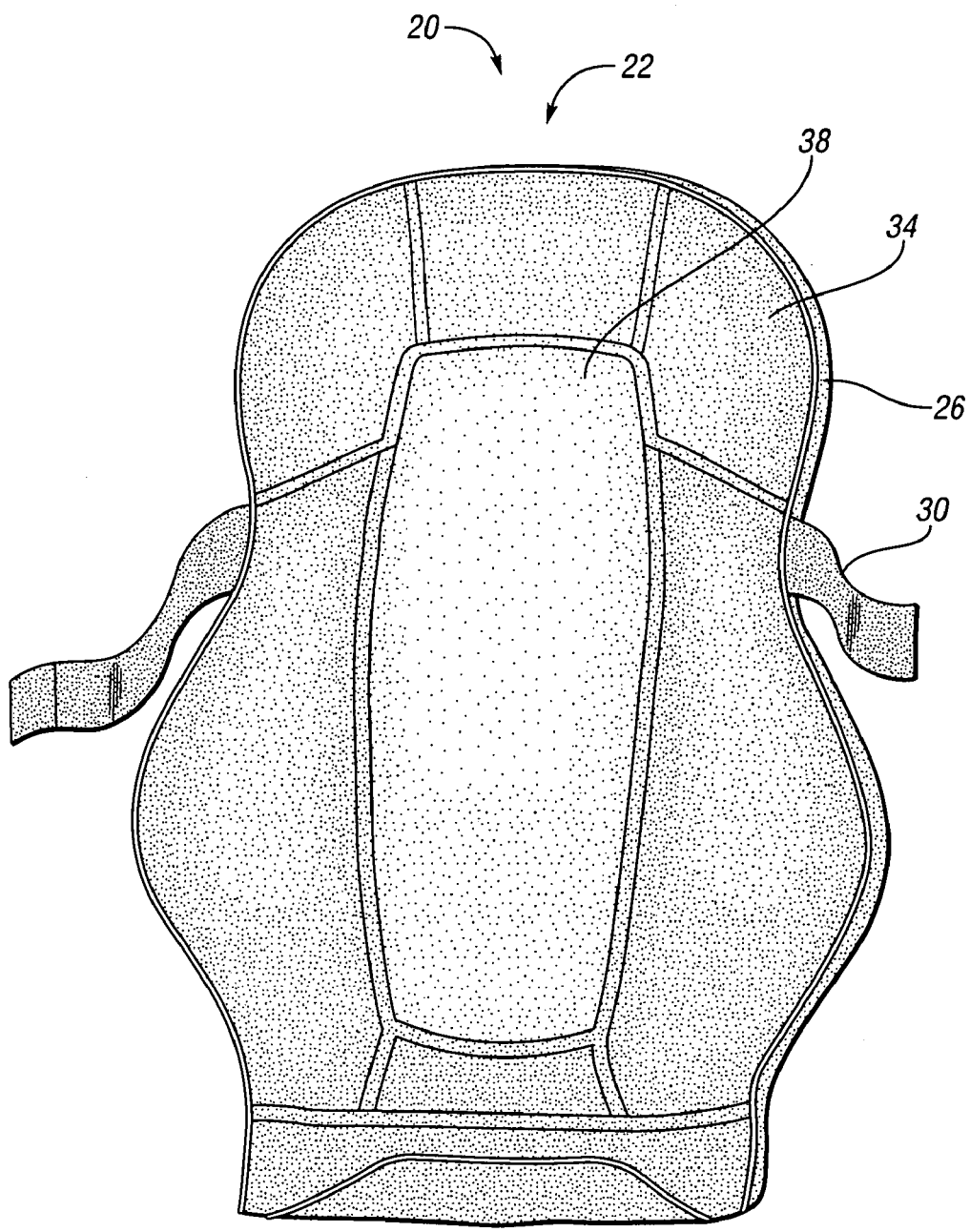
FIG. 2 is an elevation view of a backrest region of the massager of FIG. 1.

With reference to FIG. 1, an exemplary embodiment body massager is illustrated in accordance with the present invention and is referenced generally by numeral 20. The body massager 20 includes a backrest region 22 and a seat support region 24. The internal assemblies of the backrest region 22 and the seat support region 24 are collectively retained within a flexible cover 26, which is formed of a high quality vinyl. Of course, other materials such as leather may be employed for the cover 26. The cover 26 provides a pivotal connection 28 at a lower longitudinal end of the backrest region 22 and a rearmost end of the seat support region 24. The flexible material of the cover 26 provides a living hinge at the pivotal connection 28, thereby permitting user adjustment of an included angle between the backrest region 22 and the seat support region 24.

Various massage effects may be provided by the body massager 20. Such massage effects may include a rolling massage effect and/or a kneading massage effect provided in the backrest support 22. For the embodiment illustrated, the body massager 20 is operable to provide these massage effects longitudinally along the length of the backrest region 22. The seat support region 24 may also provide a massage effect such as a vibratory massage effect to the user seated upon the seat support region 24.

The backrest region 22 is sized to be received upon a backrest of a conventional chair. Likewise, the seat support region 24 is sized to be received upon a seat support of a conventional chair. Of course, the user may employ the massager 20 with or without utilization of a conventional chair, but the body massager 20 is sized to be received on a conventional chair for converting a conventional chair into a massage chair.

The body massager 20 is portable due to its compact size and light weight so that the user may place the body massager 20 upon a conventional chair for receiving a massage when seated upon the chair. The adjustability of the included angle between the backrest region 22 and the seat support region 24 accommodates a wide range of angles that may be incorporated in conventional chairs. Alternatively, the user may lay the body massager 20 flat upon an underlying surface for experiencing a massage effect in a lie down position.

The backrest region 22 includes a height and width corresponding to the conventional chair and has a thickness that is adequate for housing the massage assembly therein, while avoiding disruption of comfort and support provided by the underlying chair. Likewise, the seat support region 24 has a width and a depth corresponding to that of the conventional seat support and has a thickness that is adequate for housing an associated massage assembly, while also avoiding disruption of comfort and support provided by the underlying chair.

Additionally, the backrest region 22 includes a pair of straps 30 affixed to lateral sides of the backrest region 22 for securing the body massager 20 to the conventional chair. The straps 30 each include one of a hook and loop material for securing the straps 30 about the backrest of the conventional chair. Of course, any engagement mechanism is contemplated such as a belt buckle, a clip or the like.

The seat support region 24 includes a seating surface 32 for receiving the user when seated. The backrest region 22 includes a backrest surface 34 for receiving and supporting the back of a user. The massage assembly of the backrest region 22 imparts a massage effect through the backrest surface 34. Also, a massage assembly in the seat support region 24 may impart a massage effect through the seating surface 32.

A central region 38 of the backrest surface 34 is generally translucent, thereby permitting the user to partially view an underlying massage formation beneath the central region 38 of the cover 26. The central region 38 may be provided by a woven fabric material. By permitting the user to view the massage formation through the central region 38, the user may identify the massage effect imparted by the massager 20. Additionally, the user is provided with a visual effect provided by the operation of the massage assembly. Further, at a point of sale, where the massager 20 may be displayed without packaging, the user may visually identify the massage features of the massager 20 without further inspection of the massager 20, packaging or literature.

Referring again to FIG. 1, the body massager 20 further includes a remote 40 connected to the massager 20 for controlling the operations of the massager 20. The cover 26 is provided with a pocket 42 mounted to a lateral side of the seat support region 24. The pocket 42 has an opening provided in its rearward end so that the remote 40 may be conveniently retained when not in use.

Figure 3:
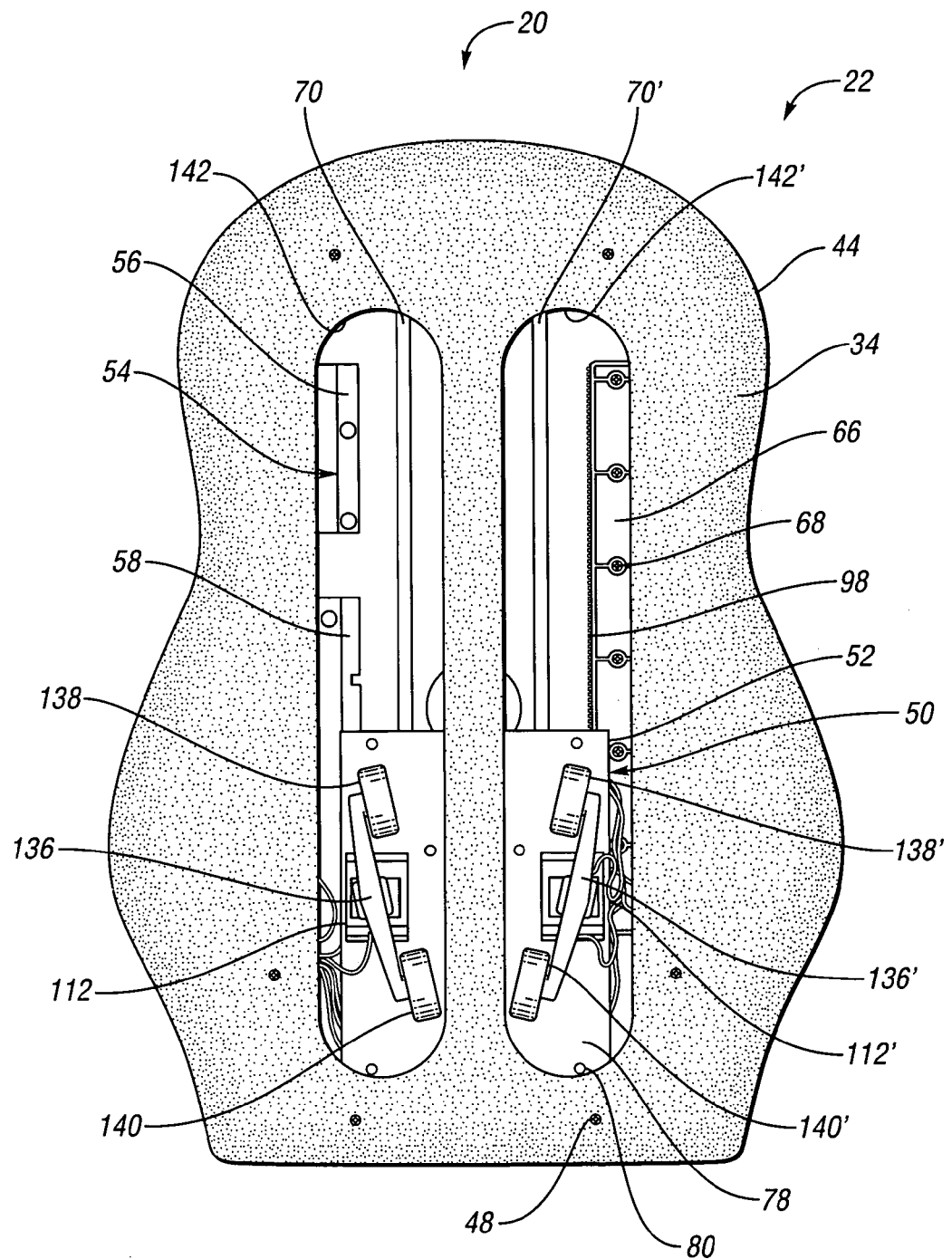
FIG. 3 is an elevation view of the backrest region of the massager of FIG. 1 including a carriage with a massage mechanism, illustrated with a cover removed therefrom.
Figure 4:
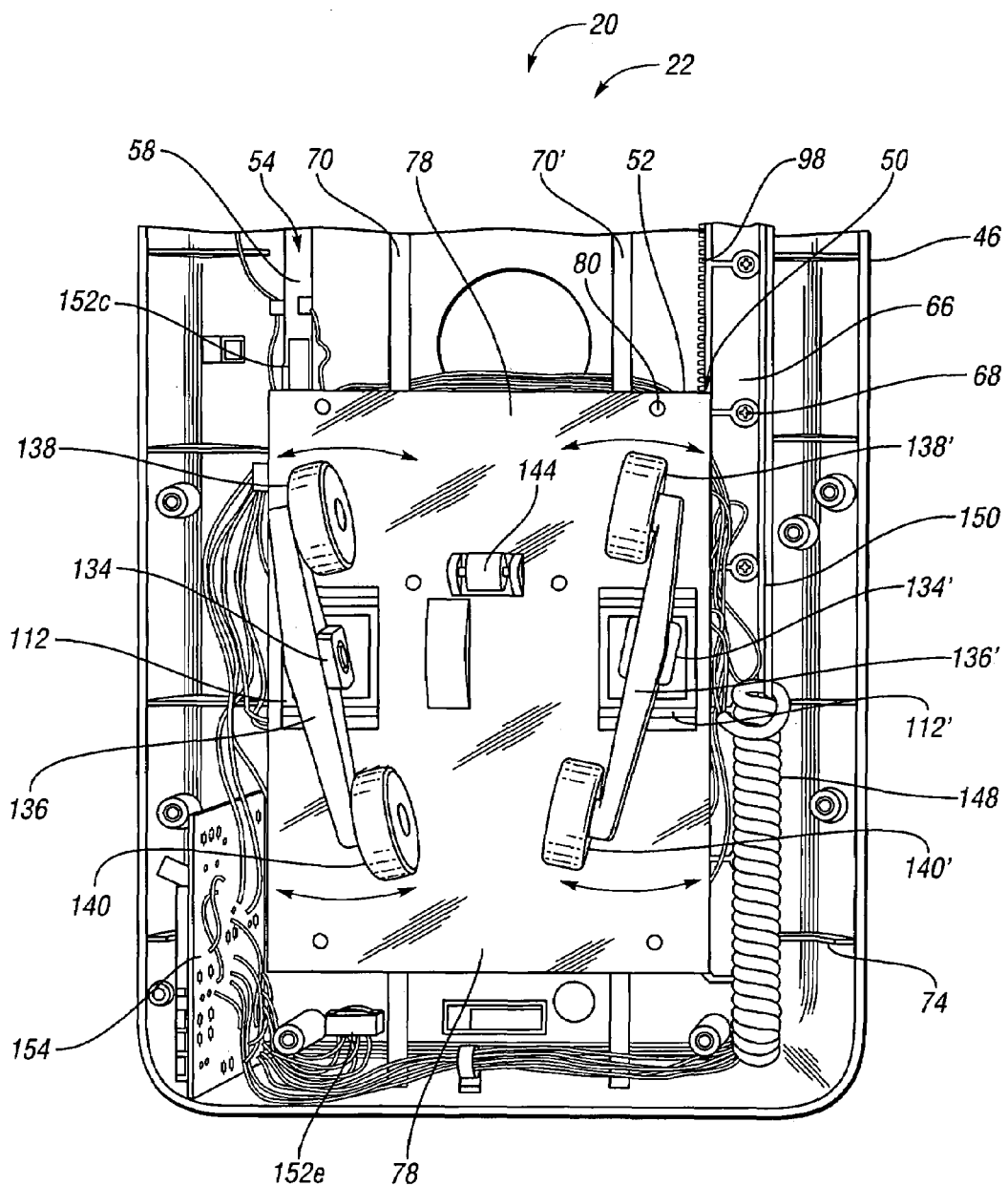
FIG. 4 is an enlarged partial elevation view of the backrest regoin of the massager of FIG. 1, illustrated with a housing portion removed therefrom for illustration of the carriage and massage mechanism.
Figure 5:
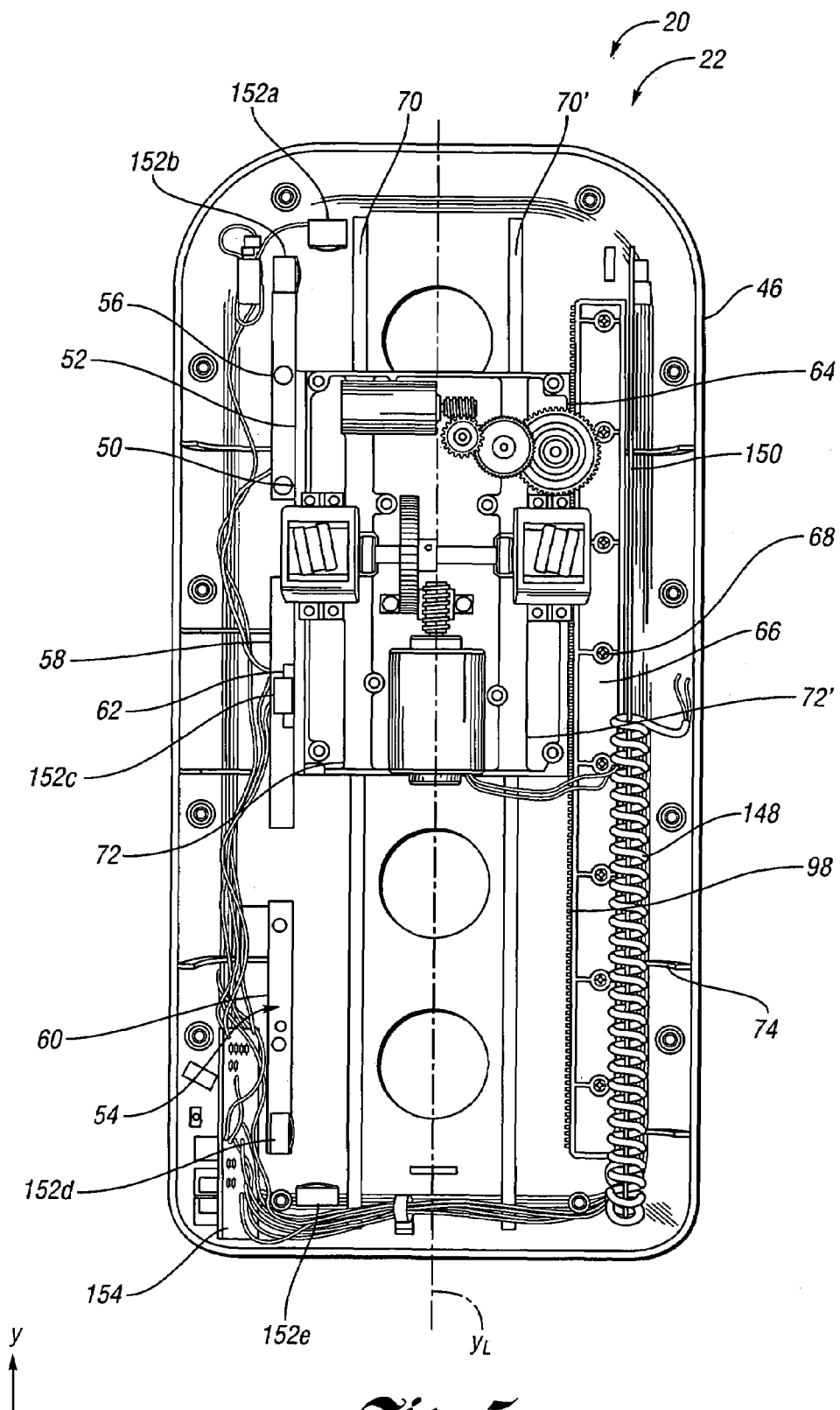
FIG. 5 is an elevation view of the backrest region of the massager of FIG. 1, illustrated with a housing portion removed therefrom, and illustrated with a cover plate removed from the carriage.

Referring now to FIGS. 3-5, the backrest region 22 is illustrated in greater detail. The backrest region 22 includes a two-piece housing provided by a forward housing portion 44 and a rearward housing portion 46. The forward housing portion 44 and the rearward housing portion 46 are sized and adaptable to be secured together by a plurality of fasteners 48 for retaining components of a massage assembly 50 therein. The massage assembly 50 includes a carriage 52 which cooperates with the rearward housing portion 46 for limited longitudinal translation within the backrest region 22. Accordingly, the rearward housing portion 46 includes a longitudinal guide 54 for cooperating with the carriage 52. The longitudinal direction y is illustrated in FIG. 5 and the housing includes a longitudinal axis $y_L$, which is also illustrated in FIG. 5.

With reference to FIG. 5, the guide 54 includes a series of gibs indicated and referenced as upper gib 56, central gib 58 and lower gib 60. The gibs 56, 58, 60 of the rearward housing portion 46 cooperate with and retain a first longitudinal key 62 formed laterally along the carriage 52. The carriage 52 includes a second longitudinal key 64 formed laterally along the carriage 52, transversely spaced from the first key 62. A transverse direction x is illustrated is illustrated in FIG. 5. The second key 64 is retained relative to the rearward housing portion 46 by an elongate retainer gib 66, which is secured to the rearward housing portion 46 by a series of fasteners 68.

The guide 54 of the rearward housing portion 46 further comprises a pair of longitudinal rails 70, 70' provided within the rearward housing portion 46. A pair of keyways 72, 72' are formed longitudinally through the underside of the carriage 52. The keyways 72, 72' are sized to receive the rails 70, 70' respectively. The cooperation of the rails 70, 70' and the keyways 72, 72' provides transverse guidance and support to the carriage 52 as it translates along the guide 54. The carriage 52 may also include a plurality of roller bearings (not shown), which are each pivotally connected to the carriage 52 and are offset from and adjacent to the keyways 72, 72' for engaging a bearing surface provided upon each rail 70, 70'. As the carriage 52 translates along the guide the 54, the carriage 52 is bearingly supported by the roller bearings as they engage the surfaces provided by the rails 70, 70'. Assignee's copending application, U.S. Ser. No. 11/205,949 entitled Portable Body Massager and filed on Aug. 17, 2005 by Roman Ferber et al., discloses and illustrates an exemplary embodiment of the cooperation of keyways, rails and roller bearings for the carriage. The Ferber 11/205,949 application is incorporated in its entirety by reference herein.

The rearward housing portion 46 includes a series of ribs 74 formed therein for providing cross support to the rearward housing portion 46 and the gibs 56, 58, 60, 66. Accordingly, the two-piece housing 44, 46 provides both a housing and a structural frame for the massage assembly 50. Both housing portions 44, 46 may each be formed from an injection molding process or the like to provide low weight, yet rigid structural members. Additionally, the upper gib 56, the central gib 58, the lower gib 60 and the rails 70, 70' may be integrally formed with the rearward housing portion 46, thereby enhancing rigidity and structural cooperation amongst these elements, while minimizing costs in components and assembly.

With reference again to FIG. 3, the forward housing portion 44 has a peripheral contour that exceeds the overall dimensions of the rearward housing portion 46. This feature provides broad lateral support to the user that is distributed directly to the rearward housing portion 46. A cushioned pad (not shown) is adhered to an external face of the forward housing portion 44 for providing padded comfort and support to the user as the user rests its back against the backrest surface 34.

Figure 6:
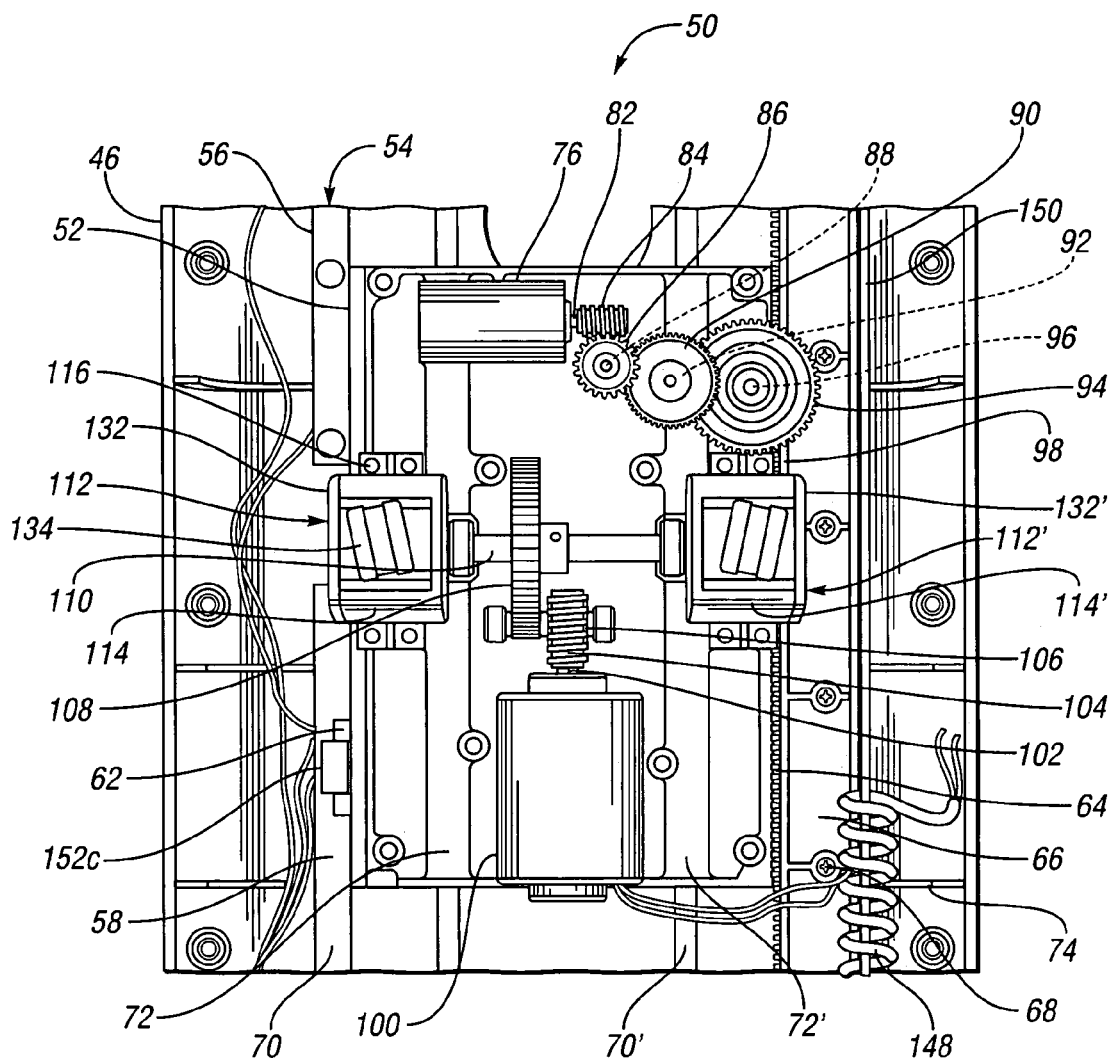
FIG. 6 is an enlarged elevation view of the backrest region of the massager of FIG. 1, illustrated with a housing portion removed therefrom and with the cover plate removed from the carriage for illustrating the massage mechanism in further detail.

With reference now to FIGS. 4 and 6, the massage assembly 50 is illustrated in greater detail. The massage assembly 50 includes a first motor 76, which is mounted to the carriage 52 and retained by a cover plate 78. The cover plate 78 and the carriage 52 collectively define a motor mount for the first motor 76 and are fastened together by a plurality of fasteners 80. The first motor 76 is operable to translate the carriage 52 along the guide 54 of the rearward housing portion 46. The first motor 76 includes a motor output shaft 82 extending from the first motor 76 and driven thereby. A worm 84 is provided on the motor output shaft 82, fixed relative to the shaft 82. The worm 84 drives a worm gear 86 that is mounted to the carriage 52 for rotation relative to the carriage 52.

A first pinion gear 88 is mounted to the underside of the worm gear 86 and is driven thereby. A first reduction gear 90 is rotatably mounted upon the carriage 52 and engaged with the first pinion gear 88. A second pinion gear 92 is formed on the underside of the first reduction gear 90. A second reduction gear 94 is also rotatably mounted to the carriage 52. The second reduction gear 94 is engaged with the second pinion gear 92. The second reduction gear 94 includes a third pinion gear 96 secured to its underside. The third pinion gear 96 engages a gear rack 98 formed along the retainer gib 66.

The worm 84, worm gear 86, first pinion gear 88, first reduction gear 90, second pinion gear 92, second reduction gear 94, third pinion gear 96 and gear rack 98 provide a transmission such that rotation from the motor output shaft 82 experiences three stages of reduction for reduced rotation and increased torque of the third pinion gear 96 relative to the motor output shaft 82. Since the rack 98 is fixed relative to the guide 54, rotation of the third pinion gear 96 translates the carriage 52 along the guide 54. Accordingly, the rotation of the motor output shaft 82 results in translation of the carriage 52 along the guide 54 due to the engagement with the gear rack 98.

The massage assembly 50 also includes a second motor 100, which is mounted to the carriage 52 and retained by the cover plate 78. The cover plate 78 and the carriage 52 collectively define a motor mount for the second motor 100, and are fastened together by the plurality of fasteners 80. The second motor 100 is operable to impart a massage effect from the massage assembly 50. The second motor 100 includes a motor output shaft 102 extending from the second motor 100 and driven thereby. A worm 104 is provided on the motor output shaft 102 and is fixed relative to the shaft 102. The worm 104 drives a helical worm gear 106 that is mounted to the carriage 52. The helical worm gear 106 drives a reduction gear 108. The reduction gear 108 is mounted to a transverse shaft 110 that is journaled to the carriage 52.

The transverse shaft 110, in turn drives a pair of oscillating mechanisms 112, 112', which each convert the rotary motion of the transverse shaft 110 into oscillation. Specifically, the oscillating mechanisms 112, 112' illustrated are often referred to as swash plate mechanisms. Although swash plate mechanisms are illustrated, the invention contemplates utilization of any mechanism that converts rotary motion to reciprocating or oscillatory motion, such as scotch yoke mechanisms, cam and follower engagements, linkages or the like.

Figure 7:
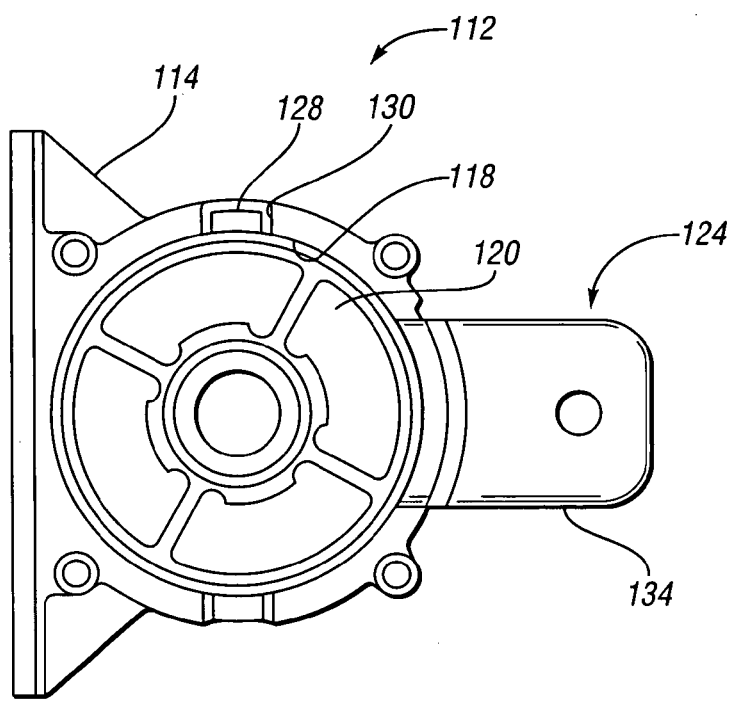
FIG. 7 is a side elevation view of an oscillating mechanism of the massage mechanism.
Figure 8:
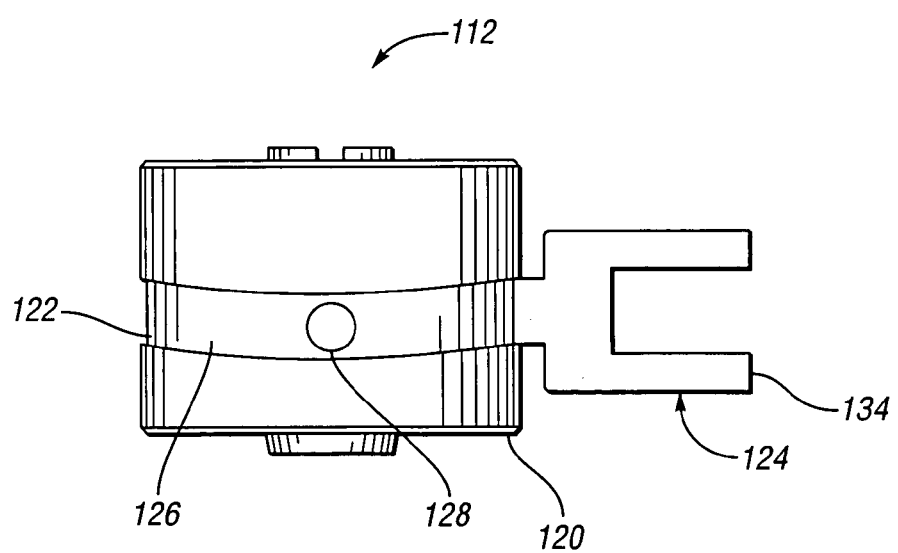
FIG. 8 is a top plan view of the oscillating mechanism of the massage mechanism of FIG. 7, illustrated removed from a housing.

Referring now to FIGS. 6-8, the oscillating mechanisms 112, 112' are illustrated in greater detail. Each oscillating mechanism 112, 112' includes a casing 114, 114' fastened to the carriage 52 by fasteners 116. Each casing 114, 114' has a bore 118 formed therein for housing the swash plate assembly. A swash guide 120 is disposed within the bore 118 and is fixed for rotation with the transverse shaft 110. The swash guide 120 has a circumferential slot 122 formed thereabout. The slot 122 has an axis that is canted relative to a plane normal to the transverse shaft 110. Thus, as the transverse shaft 110 is driven by the second motor 100, the swash guide 120 rotates relative to the carriage 52 thereby providing an oscillating effect of the slot 122 relative to the carriage 52.

A massage bracket 124 is provided having a plate 126 disposed within the slot 122 of the swash guide 120 within the casing 114. The plate 126 includes a pair of followers 128, each extending into one of a pair of transverse slots 130 formed through the casing 114. The cooperation of the followers 128 within the slots 130 prevents the plate 126 for rotating within the casing 114 about a transverse axis. Thus, the rotation of the swash guide 120 causes the plate 126 to oscillate within a plane defined by the transverse slots 130. For the illustrated embodiment, the plane of oscillation is generally parallel to the carriage 52. The oscillating mechanisms 112, 112' also each include an end cap 132, 132' fastened thereto for retaining the swash guide 120 and the plate 126 of the massage bracket 124 within each casing 114.

Each massage bracket 124 includes a fork 134 extending out of the casing 114 in a direction that is generally perpendicular to the carriage 52. Referring again to FIG. 4, a pair of massage arms 136, 136' are each pivotally connected to one of the forks 134, 134' respectively at an intermediate region of each massage arm 136, 136'. Each massage arm 136, 136' includes an upper massage roller 138, 138' and a lower massage roller 140, 140' pivotally connected thereto at its distal ends.

The massage rollers 138, 138', 140, 140' are spaced away from the carriage 52, and extend through apertures 142, 142' (FIG. 3) in the forward housing portion 44 to engage the underside of the cover 26 to thereby impart a rolling massage effect to the body of the user. With reference to FIG. 4, the second motor 100 drives the oscillating mechanisms 112, 112' such that the massage rollers 138, 138', 140, 140' oscillate relative to the carriage 52. This oscillation is illustrated by the arcuate arrows in FIG. 4. This oscillation generates a kneading effect wherein the upper massage rollers 138, 138' converge while the lower massage rollers 140, 140' diverge. Likewise, the upper massage rollers 138, 138' diverge during the oscillation while the lower massage rollers 140, 140' converge. Of course, the invention contemplates that various kneading effects may be employed and the massage rollers may be in a phase with another, or out of phase with each other, such as the asynchronous kneading effect generated by the massage assembly 50 illustrated.

The apertures 142, 142' (FIG. 3) formed through the forward housing portion 44 are generally elongate for permitting the massage rollers 138, 138', 140, 140' to pass therethrough as the carriage 52 is translated relative to the guide 54. Further, the cover plate 78 includes a roller bearing 144 (FIG. 4) pivotally connected thereupon for engaging an underside bearing surface formed within the forward housing portion 44, thus providing bearing support between the carriage 52 and the forward housing portion 44. Thus, loading imparted upon the backrest surface 34 is translated through the forward housing portion 44 to the carriage 52 through the roller bearing 144, to the rearward housing portion 46 through the roller bearings of the carriage 52 for providing bearing support therebetween and preventing such loading from inhibiting the translation of the carriage 52 along the guide 54.

Figure 9:
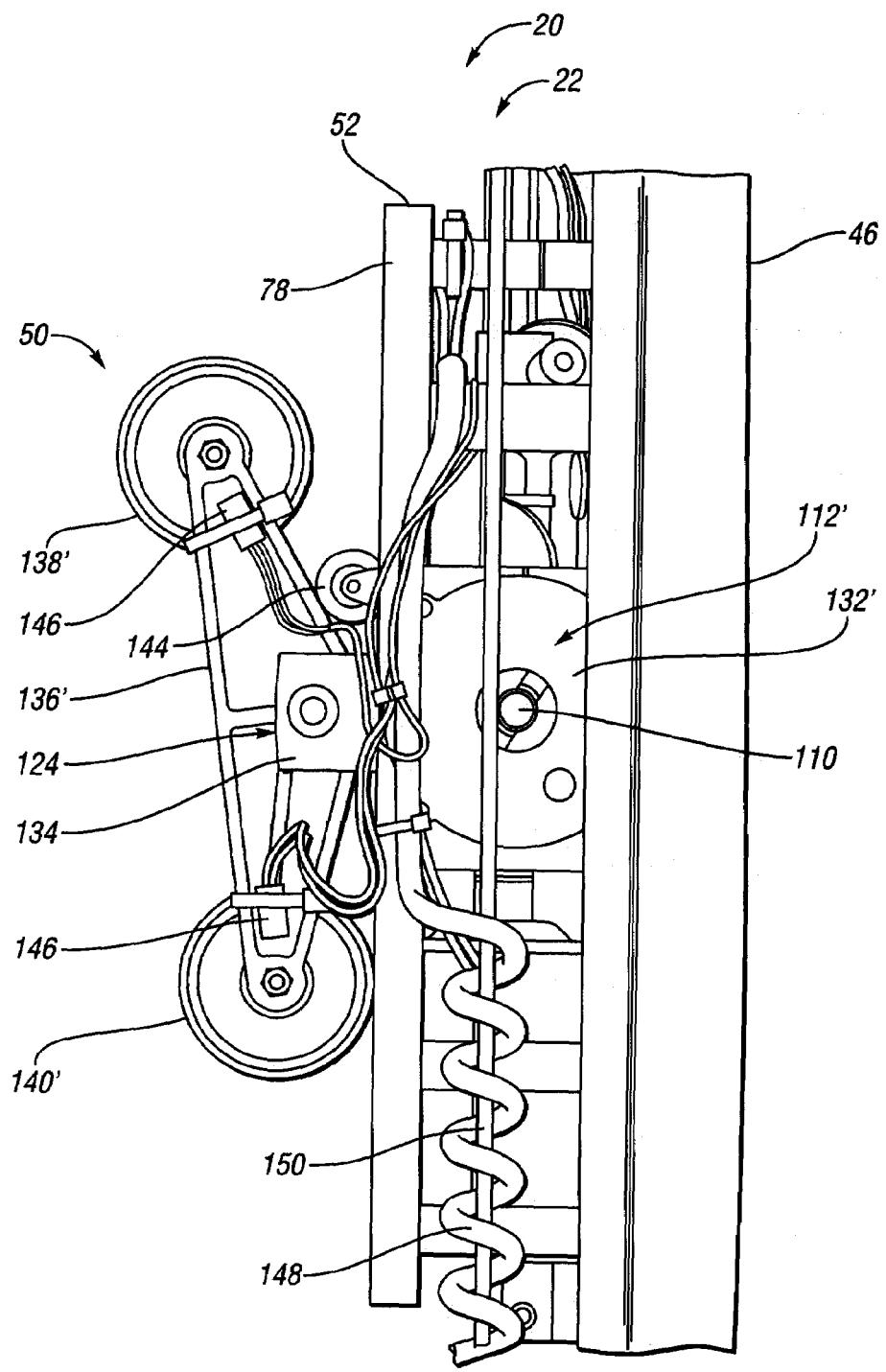
FIG. 9 is a right side elevation view of the backrest region of the massager of FIG. 1, illustrated with a housing portion removed therefrom for illustrating the carriage and massage mechanism.

An aspect of prior art massage roller assemblies is to include hard stops and biasing members in the connection between the massage arm and the massage bracket. Such mechanisms add cost to manufacturing and result in a moment applied to the oscillating mechanism. With reference now to FIG. 9, the massage rollers 138', 140' are each sized to engage the cover plate 78 upon application of a load to the given massage roller. For example, FIG. 9 illustrates the lower massage roller 140' in a loaded condition such that the lower massage roller 140' engages the cover plate 78. This loading causes the massage arm 136' to pivot relative to the cover plate 78 until the lower massage roller 140' engages the cover plate 78. The load applied to the lower massage roller 140' is distributed directly to the cover plate 78 and therefore eliminates a moment that would otherwise be applied to the massage bracket 124 and consequently the oscillating mechanism 112'.

In one embodiment of the invention, the massage arms 136, 136' are provided with light emitting diodes (LED's) 146 (FIG. 9) mounted thereto for illuminating each massage roller 138, 138', 140, 140'. The illuminated massage rollers 138, 138', 140, 140' generate a mobile illuminated visual effect through the partially transparent central region 38 of the cover 26. To further enhance the illuminated massage effect, the massage rollers 138, 138', 140, 140' are formed from a generally translucent material such that the illuminated effect from the LED's 146 illuminates each of the rollers 138, 138', 140, 140'.

The illumination of the massage rollers 138, 138', 140, 140' permits a user to experience and appreciate illuminated massage effects. Additionally, at a point of sale display wherein consumers are permitted to operate the massager 20, consumers may readily identify the number of massage contact points, the type of massage available and the various massage features. At point of sale displays, where the massager 20 may be left in continuous operation, a passerby may readily identify the various massage effects due to the illuminated massage rollers 138, 138', 140, 140'. In order to power the LED's 146, wiring is provided on the carriage 52 as illustrated in FIG. 9.

The LED's 146 are illuminated when the massage 20 is in a power-on mode. Of course, the invention contemplates that the LED's 146 may be utilized for displaying alternate illumination for alternate massage effects. For example, a pair of LED's 146 may be provided at each massage roller 138, 138', 140, 140' for displaying one illumination color during one massage effect, such as a rolling massage effect, another color for kneading massage effect, and both colors for a rolling and kneading massage effect.

The invention also contemplates that the forward housing portion 44 may be partially transparent for permitting the user to view the operation of the massage assembly 50. The invention further contemplates that the cover plate 78 may be partially transparent for permitting the user to view the operation of the components of the massage assembly 50.

The invention contemplates that the illumination effect may be provided with massagers of various contact portions and massage assemblies. For example, the illumination effect may be provided with rotary kneading massagers, such as those disclosed in Assignee's copending application Ser. No. 11/205,949, which has been incorporated by reference herein. In an embodiment of the present invention with a rotary kneading massager, in order to convey power to the LED's, conductive brushes may extend from the undersides of the massage nodes for engaging conductive contact disks provided on the cover plate of the carriage. The contact disks may be wired into a power source of the body massager.

Due to the translation of the carriage 52 and the first and second motors 76, 100, cord management may be necessary to ensure a power cord 148, which provides power to the first and second motors 76, 100 and the LED's 146, does not interfere with, nor get damaged by the operations of the massage assembly 50. Accordingly, a longitudinal bar 150 is provided within the backrest region 22 mounted to the rearward housing portion 46. The power cord 148 is coiled about the bar 150 for extension and retraction thereabout as the carriage 52 is translated along the guide 54.

The first motor 76 is directly coupled to the associated transmission for translation of the carriage 52 when the first motor 76 is powered. In order to reverse direction of the carriage 52, the rotational direction of the first motor 76 is reversed as well. In order to control the reversal of power to the first motor 76 a series of limit switches 152a-152e (FIG. 5) are provided along the guide 54. Each limit switch 152a-152e includes a leaf spring which extends in an unloaded position. Upon actuation of each leaf spring, the respective limit switch 152a-152e sends a signal indicating the presence of the carriage 52. Accordingly, the limit switches 152a-152e are each oriented so that the associated leaf spring extends into the path of travel of the carriage 52 for actuation thereby. The signals provided by the limit switches 152a-152e are processed by a central processing unit provided at a circuit board 154 mounted within the backrest region 22 to the rearward housing portion 46 as illustrated in FIG. 5.

Figure 10:
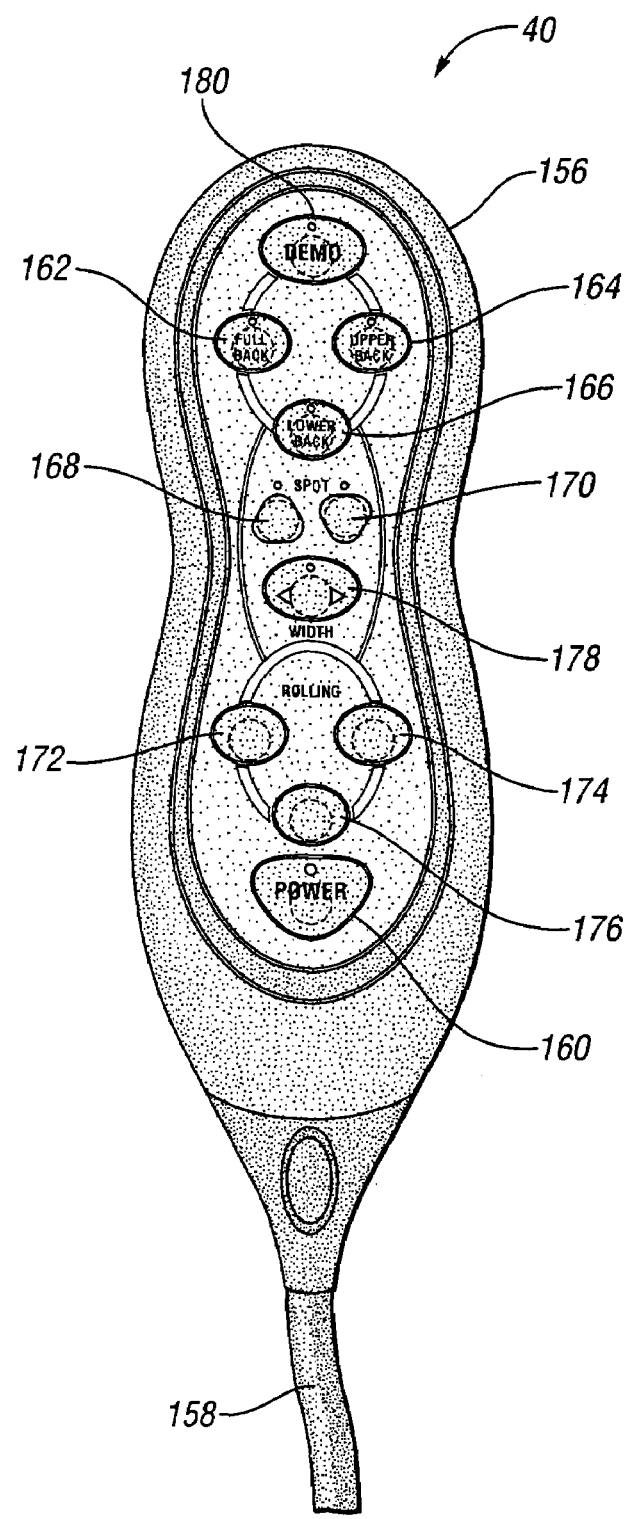
FIG. 10 is an enlarged elevation view of a control pad of the massager of FIG. 1.

The user operates the massage assembly 50 via a control pad provided on the remote 40 of the body massager 20. Referring now to FIG. 10, the remote control 40 is illustrated in greater detail. The remote control 40 includes a body 156 that is sized to be grasped by the user, and a tether 158, which secures the body 156 to the body massager 20. The remote control 40 is wired to the circuit board 154 for operable communication via the tether 158.

The remote control 40 includes a power button 160 for turning the body massager 20 on and off. Operation of the power button 160 also controls the illumination effect of the LED's 146. The remote control 40 also includes controls for the kneading massage effect and the rolling massage effect provided from the massage assembly 50. Each button on the remote control 40 includes an LED for indicating that the associated function is in operation.

A full back shiatsu massage effect button 162 is provided for selecting a kneading and rolling massage effect to the full longitudinal range of the guide 54 wherein limit switches 152a, 152b, 152d and 152e provide the range of travel for the carriage 52. In this operation, the second motor 100 is driven continuously for imparting a continuous kneading massage effect. Additionally, the first motor 76 is driven continuously for a continuous rolling massage effect due to translation of the carriage 52 along the guide 54. Upon the carriage 52 reaching a limit in the overall travel along the guide 54, limit switches 152a and 152b or limit switches 152d and 152e indicate that the limit has been reached and the circuit board 154 reverses the rotation of the first motor 76 so that the carriage 52 reverses its direction of travel along the guide 54.

An upper back shiatsu massage effect button 164 and a lower back shiatsu massage effect button 166 are also provided for controlling a kneading and rolling massage effect to a targeted range as defined by limit switches. For example, the upper back button 164 provides a kneading and rolling massage effect within a range created by limit switches 152a, 152b and 152c. The lower back shiatsu massage effect button 166 provides a rolling and kneading massage effect between limit switches 152c and 152d, 152e. In each of these ranges, the second motor 100 is driven continuously for providing a kneading massage effect; and the first motor 76 is driven continuously for translating the carriage 52 within the range. Upon the carriage 52 reaching a limit within the range, the rotation of the first motor 76 is reversed thereby reversing the direction of the carriage 52.

The remote control 40 further includes an upward targeted kneading massage effect button 168 and a downward targeted kneading massage effect button 170 for providing the kneading massage effect to a targeted region upon the user's body. Upon actuation of one of these buttons 168, 170 the second motor 100 is driven continuously for providing a continuous kneading massage effect. As either of these buttons 168, 170 is depressed by the user, the first motor 76 is driven in a direction corresponding to the depressed button 168, 170 for translating the carriage 52 to a user selected orientation. Upon reaching the user selected position, the user removes his or her finger from the button 168, 170 thereby discontinuing operation of the first motor 76 so that the carriage 52 stops at the selected position, while the second motor 100 continues to drive the kneading massage effect.

A full back rolling massage effect button 172 is provided on the remote control 40 for providing a full rolling massage effect between limit switches 152a, 152b and 152d, 152e. For this effect, the first motor 76 is driven continuously and the second motor 100 is not driven so that the massage arms 136, 136' are stationery in orientation relative to the carriage 52 for rolling the massage rollers 138, 138', 140, 140' relative to the carriage 52 for providing a rolling massage effect upon the body of the user. The first motor 76 is driven in a first rotary direction until the carriage 52 engages the limit switch within the range of travel. Upon reaching this limit, the rotation of the first motor 76 is reversed thereby reversing the direction of the carriage 52.

An upper back rolling massage effect button 174 and a lower back rolling massage effect button 176 are also provided for generating the rolling massage effect within a targeted range as set forth by limit switches 152a, 152b and 152c for the upper back button 174, and limit switches 152c and 152d, 152e for the lower back button 176.

A width adjustment button 178 is also provided on the remote control 40 so that while a user is experiencing a rolling massage effect, as selected by one of the rolling massage effect buttons 172, 174, 176, the user may adjust the width of the massage rollers 138, 138', 140, 140'. Specifically, the width adjustment button 178 controls the operation of the second motor 100 for the user selected duration. Upon releasing the width adjustment button 178, the operation of the second motor 100 is discontinued.

The width adjustment button 178 permits the user to adjust the oscillation orientation of the massage rollers 138, 138', 140, 140' as the carriage 52 is driven along the guide 54. This oscillation adjustment of the massage rollers 138, 138', 140, 140' thereby adjusts the relative width of the rollers 138, 138', 140, 140' relative to the longitudinal axis $y_L$.

The remote control 40 further includes a demo button 180 for providing a demonstration operation of various combinations of the massage effects provided by the kneading and rolling buttons 162-178 so that the user experiences a variety of massage effects.

Briefly, the massage effects are generated from the simplified massage assembly 50. Kneading massage effects and width adjustment of the rolling massage effects are provided from a common motor by continuous or user selected oscillation of the massage rollers 138, 138', 140, 140'. Accordingly, width adjustment of the rollers 138, 138', 140, 140' is provided within the massager 20 without limiting the portability and weight of the massager 20 and without requiring a third motor.

The remote control 40 may also include a seat massage button for imparting a massage effect to the seat support region 24. As disclosed in Assignee's Ferber et al. U.S. patent application Ser. No. 10/836,905, vibratory massage assemblies may be provided within the seat support region 24. The Ferber et al. Ser. No. 10/836,905 application is incorporated in its entirety by reference herein.

In summary, the massager 20 provides an illuminated massage effect to provide a visually appealing effect in combination with the associated massage effect. Such illumination may attract attention of consumers, while visually identifying associated massage features to the user. Further, the body massager 20 includes a simplified massage effect, in comparison to prior art massagers, thereby lending to portability of the massager and facilitating cost effectiveness.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A massage apparatus comprising:
   a housing;
   a massage formation provided on the housing for contacting a body part of a user;
   a massage mechanism oriented within the housing for imparting a massage effect to the massage formation for massaging the body part;
   a light source provided on the massage formation for conveying an illumination effect from the massage formation;
   a carriage oriented in the housing for limited translation in the housing, wherein the massage formation is provided on the carriage;
   a motor supported upon the carriage;
   a shaft mounted on the carriage and operably driven by the motor for rotation about an axis, the shaft having a pair of oscillating mechanisms each having a portion that is canted relative to the shaft axis;
   a pair of massage brackets each journalled to one of the oscillating mechanisms and engaging the carriage for limited rotation about the shaft axis such that rotation of the shaft oscillates the massage brackets relative to the carriage;
   a pair of massage arms each pivotally connected to one of the massage brackets; and
   a pair of massage rollers each pivotally connected to one of the massage arms for imparting a rolling massage effect upon the portion of the user's body as the carriage is translated relative to the housing and for imparting a kneading massage effect upon the portion of the user's body as the massage brackets oscillate relative to the carriage; wherein the pair of massage rollers are generally translucent and the light source is provided adjacent to at least one of the massage rollers for conveying the illumination effect through the at least one massage roller.

2. The massage apparatus of claim 1 wherein the light source further comprises at least one light emitting diode.

3. The massage apparatus of claim 1 wherein the light source indicates a mode of massage operation of the massage mechanism.

4. The massage apparatus of claim 1 further comprising a cover over the massage formation that is generally translucent for conveying the illumination effect through the massage surface.

5. The massage apparatus of claim 1 wherein the massage formation further comprises generally translucent contact portions and the light source is provided adjacent to at least one of the contact portions for illuminating the contact portion.

6. The massage apparatus of claim 1 wherein the housing is sized to be received and supported by a backrest of a conventional chair.

7. The massage apparatus of claim 1 wherein the pair of massage rollers are generally translucent and the light source is provided on one of the massage arms for conveying the illumination effect through at least one roller.

8. The massage apparatus of claim 1 wherein each pair of massage rollers further comprises a first massage roller and a second massage roller each rotatably mounted on opposed sides of the pivotal connection of the corresponding massage arm and massage bracket.

9. The massage apparatus of claim 8 wherein the massage rollers are oriented to engage the carriage upon application of a load imparted to the rollers to distribute the load to the carriage.

10. The massage apparatus of claim 8 wherein the massage rollers are generally translucent and the light source further comprises a plurality of light emitting diodes each mounted to one of the massage arms facing one of the massage rollers for illuminating the massage rollers.

11. The massage apparatus of claim 10 further comprising a flexible cover mounted to the housing wherein the massage rollers engage the flexible cover, the flexible cover being at least partially translucent so that a user may view the illuminated massage rollers.

12. A body massager comprising:
- a housing having a longitudinal axis and a partially translucent external contact surface for receiving a portion of a body of a user;
- a longitudinal guide mounted in the housing;
- a carriage oriented in the housing and cooperating with the guide for limited longitudinal translation in the housing along the guide;
- a first motor supported by one of the housing and the carriage, the first motor having a motor output shaft driven thereby, the motor output shaft being operably coupled to the carriage and the housing to translate the carriage along the guide;
- a second motor supported by one of the housing and the carriage, the second motor having a motor output shaft driven thereby;
- a transverse shaft mounted on the carriage and operably coupled to the motor output shaft of the second motor for rotation about a transverse axis, the transverse shaft having a pair of secondary shaft portions spaced transversely about the longitudinal axis, the oscillating mechanisms each being canted relative to the transverse axis;
- a pair of massage brackets each journalled to one of the oscillating mechanisms and engaging the carriage for limited rotation about the transverse axis such that rotation of the transverse shaft oscillates the massage brackets relative to the carriage;
- a pair of massage arms each pivotally connected to one of the massage brackets; and
- a pair of massage rollers each pivotally connected to one of the massage arms for imparting a rolling massage effect upon the portion of the user's body as the carriage is translated relative to the housing and for imparting a kneading massage effect upon the portion of the user's body as the massage brackets oscillate relative to the carriage, the massage rollers being oriented to engage the carriage; wherein the light source is supported by the carriage for illuminating one of the pair of massage rollers for conveying an illumination effect from illuminated massage roller upon application of a load imparted to the rollers to distribute the load to the carriage.

13. The body massager of claim 12 further comprising:
- a worm mounted to and driven by the first motor output shaft;
- a worm gear rotatably mounted to the carriage and operably driven by the worm;
- a pinion gear rotatably mounted to the carriage and operably driven by the worm gear; and
- a longitudinal rack affixed to the housing and engaged with the pinion gear such that rotation of the pinion gear translates the carriage along the guide.

* * * * *